(12) United States Patent
Amino et al.

(10) Patent No.: US 7,935,377 B2
(45) Date of Patent: May 3, 2011

(54) CRYSTALS OF FREE (2R, 4R)-MONATIN AND USE THEREOF

(75) Inventors: Yusuke Amino, Kawasaki (JP); Kazuko Hirasawa, Kawasaki (JP); Kenichi Mori, Kawasaki (JP); Tadashi Takemoto, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 903 days.

(21) Appl. No.: 10/860,018

(22) Filed: Jun. 4, 2004

(65) Prior Publication Data

US 2005/0272939 A1 Dec. 8, 2005

(51) Int. Cl.
*A23L 1/236* (2006.01)
*A61K 31/40* (2006.01)

(52) U.S. Cl. ........................ 426/548; 514/419

(58) Field of Classification Search .................. 426/548; 514/419
See application file for complete search history.

(56) References Cited

U.S. PATENT DOCUMENTS

| | | | |
|---|---|---|---|
| 3,615,807 A | 10/1971 | Yates | |
| 3,674,776 A | 7/1972 | Long et al. | |
| 3,772,028 A | 11/1973 | Fico et al. | |
| 3,954,816 A | 5/1976 | Bloom et al. | |
| 4,066,676 A | 1/1978 | Bloom et al. | |
| 4,975,298 A | 12/1990 | Van Wyk et al. | |
| 5,128,164 A | 7/1992 | Van Wyk et al. | |
| 5,128,482 A | 7/1992 | Olivier et al. | |
| 5,994,559 A * | 11/1999 | Abushanab et al. | 548/495 |
| 7,241,599 B2 | 7/2007 | Sugiyama et al. | |
| 7,244,462 B2 | 7/2007 | Amino et al. | |
| 7,351,569 B2 | 4/2008 | Sugiyama et al. | |
| 7,371,549 B2 | 5/2008 | Sugiyama et al. | |
| 7,378,508 B2 | 5/2008 | Chiu et al. | |
| 7,390,909 B2 | 6/2008 | Kawahara et al. | |
| 7,396,941 B2 * | 7/2008 | Mori et al. | 548/495 |
| 7,402,412 B2 | 7/2008 | Sugiyama et al. | |
| 7,432,100 B2 | 10/2008 | Sugiyama et al. | |
| 7,662,596 B2 | 2/2010 | Sugiyama et al. | |
| 7,674,915 B2 * | 3/2010 | Amino | 548/495 |
| 2003/0228403 A1 | 12/2003 | Amino et al. | |
| 2005/0118317 A1 | 6/2005 | Amino et al. | |
| 2006/0014819 A1 | 1/2006 | Mori et al. | |
| 2006/0154343 A1 | 7/2006 | Mori et al. | |
| 2007/0072277 A1 | 3/2007 | Sugiyama et al. | |
| 2008/0091032 A1 | 4/2008 | Kawahara et al. | |
| 2008/0193975 A1 | 8/2008 | Sugiyama et al. | |
| 2008/0193984 A1 | 8/2008 | Sugiyama et al. | |
| 2008/0207920 A1 | 8/2008 | Kawahara et al. | |
| 2008/0318290 A1 | 12/2008 | Sugiyama et al. | |
| 2009/0259052 A1 | 10/2009 | Kawahara et al. | |
| 2009/0318528 A1 | 12/2009 | Mori et al. | |
| 2010/0184165 A1 | 7/2010 | Sugiyama et al. | |

FOREIGN PATENT DOCUMENTS

| | | | |
|---|---|---|---|
| EP | 0 438 314 A1 | | 7/1991 |
| EP | 1 533 300 | | 5/2005 |
| GB | 2 205 834 A | | 12/1988 |
| JP | 2002-60382 | * | 2/2002 |
| JP | 2003-171365 | | 6/2003 |
| WO | 03/045914 | * | 6/2003 |
| WO | 03/045914 A1 | * | 6/2003 |
| ZA | 87/4288 | | 6/1987 |
| ZA | 88/4220 | | 6/1988 |

OTHER PUBLICATIONS

JP 2002-060382 translation, Feb. 2002, 27 pages.*
Robert Vleggaar, et al., "Structure Elucidation of Montain, a High-intensity Sweetner Isolated from the Plant Schlerochiton Ilicifolius," J. Chem. Soc., Perkin Trans., 1992, 3095-3098.
Kozo Nakamura, et al., "Total Synthesis of Montain," Organic Letters, vol. 2, No. 19, 2000, pp. 2967-2970.
Karl Bischofberger, et al., "A Simple Cycloaddition Approach to a Racemeate of the Natural Sweetner Montain," Synthetic Communications, 1994, pp. 3197-3211.
U.S. Appl. No. 11/627,700, filed Jan. 26, 2007, Amino, et al.
U.S. Appl. No. 11/505,997, filed Aug. 18, 2006, Mori, et al.
U.S. Appl. No. 12/613,713, filed Nov. 6, 2009, Kawahara, et al.
U.S. Appl. No. 12/613,839, filed Nov. 6, 2009, Sugiyama, et al.
Interference No. 105,696, Jun. 25, 2009, Kawahara, et al.
U.S. Appl. No. 12/768,360, filed Apr. 27, 2010, Sugiyama, et al.
U.S. Appl. No. 12/758,433, filed Apr. 12, 2010, Sugiyama, et al.
U.S. Appl. No. 12/108,889, filed Apr. 24, 2009, Sugiyama, et al.
U.S. Appl. No. 12/825,886, filed Jun. 29, 2010, Amino, et al.
U.S. Appl. No. 12/853,844, filed Aug. 10, 2010, Sugiyama, et al.
R.A. Sheldon, *Chirotechnology*, Marcel Dekker, NY, 1993, pp. 174-175.
V. A. Kireev, Course of Physical Chemistry, Moscow, Goskhlmizdat, 1956, p. 169.
N.I. Gelperin, Basic Processes and Apparatuses of Chemical Engineering. Moscow, Khimiya, 1981, Book 2, p. 679.
Nippon Nogei Kagaku Kaishl, (2000), 74 (special extra issue), Koen Yoshishu, p. 221.
Abushanab et al. 1999, CAS: 131:351675.
Berge et al., 1977, Journal of Pharmaceutical Science, pp. 1-19.

* cited by examiner

*Primary Examiner* — Leslie Wong
(74) *Attorney, Agent, or Firm* — Oblon, Spivak, McClelland, Maier & Neustadt, L.L.P.

(57) ABSTRACT

A crystal of free (2R,4R)-monatin is useful as a sweet substance. The crystals resist absorption of water even under high humidity, are stable and exhibit a high degree of sweetness. Thus, such crystals may used as a sweetening agent or an ingredient thereof, and as an ingredient for imparting sweetness to foods and beverages.

25 Claims, 6 Drawing Sheets

CRYSTALS OF FREE (2R, 4R)-MONATIN AND USE THEREOF

BACKGROUND OF THE INVENTION

1. Field of the Invention

The present invention relates to crystals of the (2R,4R) stereoisomer of monatin and the use thereof. More particularly, the present invention relates to crystals of free (2R,4R)-monatin, i.e., (2R,4R)-monatin in the free (non-salt) form, which is a non-naturally occurring stereoisomer of the naturally occurring (2S,4S) stereoisomer, and which is excellent as a sweetening agent or an active ingredient (sweetener) thereof. The present invention further relates to crystals of a mixture of free (2R,4R)-monatin with at least one other type of monatin stereoisomer and the use of such crystals. The present invention particularly relates to crystals of a mixture of free (2R,4R)-monatin with at least one other type of monatin stereoisomer, such as (2S,4S)-monatin, (2S,4R)-monatin, and (2R,4S)-monatin. The present invention does not relate to a crystal of a mixture of free (2S,4S)-monatin and free (2R, 4R)-monatin in a molar ratio of 1:1.

2. Discussion of the Background

As a result of modern eating habits, obesity, arising from the excessive ingestion of sugars, and the various diseases accompanied thereby have become problems of medical and social importance. Accordingly, there has been a strong demand for the development of a low calorie sweetener to replace sugar. Many various properties and requirements, such as low calorie content, safety, stability to heat and acid, sweetness quality, and cost, in addition to sweetness intensity, have been demanded for such sweetening agents.

At present, various kinds of sweetening agents have been used or proposed. For example, aspartame, which is excellent in safety and sweetness quality, and has a strong sweetness intensity (degree of sweetness), has come into practical use as a sweetening agent capable of industrial mass production and has been widely used. Thaumatin, glycyrrhizin, stevioside, and the like, which exist naturally, can be collected in large amounts and are derived from plants, are currently used as natural sweetening agents. Under such circumstances, development of a sweet substance, which has a strong degree of sweetness, for practical use as a sweetening agent has been required.

Monatin is a naturally occurring amino acid derivative isolated from the bark of the roots of *Schlerochiton ilicifolius*, which is a plant naturally grown in the area of the northwestern Transvaal of South Africa. The structure of monatin has been reported as (2S,4S)-2-amino-4-carboxy-4-hydroxy-5-(3-indolyl)-pentanoic acid[((2S,2S)-4-hydroxy-4-(3-indolylmethyl))-glutamic acid (see, Vleggaar, R. et al., *J. Chem. Soc. Perkin Trans.*, pp. 3095-3098 (1992) (Vleggaar, R. et al.) and refer to the structural formula (1) described below for its structure). Vleggaar et al. reported the sweetness intensity of this (2S,4S) substance (natural type monatin) derived from the natural plant to be 800 to 1400 times that of sucrose.

The information for monatin is summarized as follows.

Although several synthetic methods have been reported for producing monatin, many of them afford a mixture of stereoisomers. There has been nearly no report where each of the four stereoisomers having the same chemical structural formula as that of natural monatin is synthesized and isolated as a pure substance and the properties thereof investigated in detail. For synthetic examples of monatin, see: (1) Republic of South Africa Patent Application No. 87/4288 (van Wyk, P. J. et al., ZA 87/4288); (2) Republic of South Africa Patent Application No. 88/4220 (van Wyk. P. J. et al., ZA 84/4220); (3) U.S. Pat. No. 5,994,559 (Abushanab, E. et al., U.S. Pat. No. 5,994,559 (1999)); (4) Holzapfel et al., *Synthetic Communications*, vol. 24 (22), pp. 3197-3211 (1994) (Holzapfel et al.); and (5) Nakamura, K. et al., *Organic Letters*, vol. 2, pp. 2967-2970 (2000) (Nakamura, K. et al.).

As for the relationships of the stereochemistry and the sweetness intensity of monatin, van Wyk, P. J. et al., ZA 87/4288 and van Wyk, P. J. et al., ZA 84/4220, in which this issue was noted for the first time, reported that the stereoisomer present in nature and having a strong sweet taste is the (2S,4S) substance or the (2R,4R) substance based on an X-ray crystal structure analysis. It was also reported that there is a high probability that the stereoisomer present in nature and having a strong sweet taste is the (2S,4S) substance, based on the results of the synthesis of a mixture of the (2S,4S) substance and the (2S,4R) substance from (2S)-aspartic acid. Vleggaar, R. et al., mentioned above, has reported that (2S,4S)-monatin is the only stereoisomer (stereo structure) of monatin present in natural plants and its sweetness intensity is 800 to 1400 times that of sucrose. Based on this information, it was reasonable to conclude that the naturally occurring monatin stereoisomer (stereo structure) which exhibits a strong sweetness is the (2S,4S) substance.

Nakamura, K. et al., cited above, reported the isolation of hydrochloride salts of (2S,4S)-monatin and of (2S,4R)-monatin, and that, with regard to the intensity of sweet taste thereof, the synthetic (2S,4S)-monatin exhibited a sweetness potency equivalent to that of the natural specimen of monatin (the (2S,4S) substance) and that the synthetic (2S,4R)-monatin exhibits a slightly sweet taste presumably due to (2S,4S)-monatin, which is thought to be present as an impurity. However, the specific intensity of the sweet taste for (2S,4S)- and (2S,4R)-monatin was not reported. Thus, this reference is the first case in which the sweetness intensity of a non-naturally occurring stereoisomer (other than (2S,4S)) of monatin was noted, but it was reported that there was almost no sweetness in the hydrochloride salt of (2S,4R)-monatin.

Meanwhile, selective synthetic methods for the respective stereoisomers of monatin as sweeteners have been reported (see, Kitahara, T. et al., Annual Meeting in 2000, Abstracts of Papers, 3B128β (page 221), Japan Society for Bioscience, Biotechnology and Agrochemistry (Kitahara, T. et al.), but the degree of sweetness of each stereoisomer has not been reported.

Thus, with respect to the relationships between the stereochemistry and the sweetness intensity of monatin, the following has been found:

1) The naturally occurring monatin stereoisomer (stereo structure) with a sweetness intensity of 800 to 1400 times that of sucrose is the (2S,4S) substance; and 2) Although small amounts of a portion of the other non-naturally occurring stereoisomers of monatin have been isolated, there is no example in which a pure substance has been isolated, purified, and the intensity of its sweetness assessed.

That is, up to the present, with respect to the sweetness intensity of each isomer of monatin at a practical use concentration corresponding to a sucrose concentration of 5 to 10%, there has been no definite data except those of the naturally occurring monatin, i.e., the (2S,4S) substance. Therefore, it could not have been known from the existing references and patent literature references whether the non-naturally occurring stereoisomers of monatin other than (2S,4S)-monatin are usable as sweetening agents. In other words, except for the naturally occurring (2S,4S)-monatin, reliable information for the degree of sweetness (sweetness intensity) has been poor, and thus, in consideration of the totality of the prior art, one could not help but think that the non-naturally occurring monatin isomers, i.e., those other than (2S,4S)-monatin, would have a low degree of sweetness and would not be expected to be useful as sweeteners.

One reason for this conclusion is that a method for synthesizing and isolating/purifying the above various isomers has not been found. Specifically, to assess the utility of (2S,4S)-monatin and the stereoisomers thereof (i.e., the non-naturally occurring stereoisomers) as sweetening agents and to consequently develop a useful sweetening agent comprising such an ingredient, it is necessary to isolate and purify at least several hundred milligrams of naturally occurring monatin as well as the three non-naturally occurring stereoisomers thereof as purified compounds and to study the optical purity and sweetness intensity of those compounds.

To accomplish the above purpose, a method for separating and obtaining the various isomers of monatin in high purity is necessary, and as one possible method, there is the method of crystallization. Based on a search of prior patents and references, the information on crystals of monatin (including forms of free compounds, salts, and the like) is as follows.

In Vleggaar, R. et al., mentioned above, it has been reported that crystals of the free compound of monatin, the (2S,4S) substance, are obtained from a mixed solvent of water, acetic acid, and ethanol (1:1:5), and have a melting point of from 216° C. to 220° C. Also, in van Wyk, P. J. et al., ZA 87/4288 and van Wyk, P. J. et al., ZA 84/4220, it has been described that the melting point of the free compound of monatin, the (2S,4S) substance, (crystalline solid) is from 247° C. to 265° C. (decomposition), but it has also been reported that various salts are amorphous solids. In Holzapfel, C. W. et al., mentioned above, it has been reported that crystals of free compound of a mixture of synthetic (2S,4S)-monatin and (2R,4R)-monatin are obtained from a mixed solvent of water and acetic acid (10:1) by crystallizing twice, and that its melting point is from 212° C. to 214° C.

Therefore, except for these three cases with respect to the free compound of the (2S,4S)-monatin substance, concerning non-naturally occurring stereoisomers of monatin and mixtures of those multiple stereoisomers there of, free compounds thereof as a matter of course and various salts thereof have not been isolated in the crystalline state. Therefore, the physical properties and other information are not known at all. That is, with respect to monatin, there is no report of a crystallization method (which is the simplest and most effective method for purification compared with conventional purification methods such as an ion exchange chromatography) or findings for crystals obtained therefrom, other than only two cases for a free form compound of (2S,4S)-monatin and a mixture of free form compounds of (2S,4S)-monatin and (2R,4R)-monatin, and, in particular, no findings have been reported for crystals of salts.

Taking into account the above information, the present inventors separated four stereoisomers of monatin, and evaluated the degree of sweetness of the sodium salt of each stereoisomer using a 5% sucrose solution as a control. As a result, it has been demonstrated that the degree of sweetness is 50 times for a (2S,4S)-monatin substance, 300 times for a (2S,4R)-monatin substance, 2700 times for a (2R,4R)-monatin substance, and 1300 times for a (2R,4S)-monatin substance, and that (2R) monatin substances are excellent in the degree of sweetness and useful as a sweetening agent (see, PCT International Application Publication No. 03/045914 (Amino, Y. et al., WO 2003045914 A1)). In Amino, Y. et al., WO 2003045914 A1, a salt crystal of each stereoisomer was obtained as a novel substance, and was found to be excellent as a sweetening agent in terms of being thoroughly soluble in water and easily separated/purified. Furthermore, it has been found that such a salt crystal has superiority in terms of storage stability under high temperature conditions as a crystal, compared to a crystal of free (2R,4R)-monatin prepared according to the preparation method of a crystal of free (2S,4S)-monatin publicly known in Vleggaar, R. et al., noted above (see, Amino, Y. et al., WO 2003045914 A1).

In this way, the inventors prepared salt crystals of the monatin stereoisomers as novel substances, and showed the usefulness thereof in Amino, Y. et al., WO 2003045914 A1. At that time, in order to compare the natures of the various salt crystals to those of the crystals of the free compounds, crystals of free (2R,4R)-monatin were prepared according to the method described in Vleggaar, R. et al., noted above (see, Comparative Example 1 of Amino, Y. et al., WO 2003045914 A1). Since this crystal of free (2R,4R)-monatin is an enantiomer of the crystal of free (2S,4S)-monatin described in Vleggaar, R. et al., they were expected to have the same physical properties. However, the crystal of free (2R,4R)-monatin prepared by the inventors obviously had different physical properties from those of the crystal of free (2S,4S)-monatin cited in Vleggaar, R. et al., and raised the possibility that it is a novel crystal (form). That is, the melting point of the crystal of free (2R,4R)-monatin, which should have the same value as that of the crystal of free (2S,4S)-monatin described in Vleggaar, R. et al., was 175.2 to 176.1° C., which was far from the melting point of the crystal of free (2S,4S)-monatin described in Vleggaar, R. et al., 216 to 220° C. As described below, remeasuring the melting point of the crystal of free (2R,4R) monatin substance gave a value of from 171.5 to 172.7° C., which nearly reproduced the value in Comparative Example 1 of Amino, Y. et al., WO 2003045914 A1.

Therefore, it was desired to examine the preparation of crystals of free (2R,4R)-monatin and the resultant crystals of free (2R,4R)-monatin in further detail, and clarify whether this is a different crystal or crystal form from the crystal of free (2S,4S)-monatin reported in Vleggaar, R. et al., as well as to investigate the usefulness thereof as a sweetening agent.

SUMMARY OF THE INVENTION

As noted above, the inventors have already discovered that a crystal of a salt of (2R,4R)-monatin is far superior in sweetness intensity and other points as a sweetening agent than the publicly-known naturally occurring free compound of (2S,4S)-monatin (crystal). However, an object of the present invention is to provide (2R,4R)-monatin in a form other than a salt crystal (i.e., a crystal of a salt) as a sweet substance which has a strong sweetness intensity for practical use as a sweetening agent. Specifically, the objects are to find a crystal or crystal form of free (2R,4R)-monatin with physical properties (melting point, infrared absorption spectrum, powder X-ray pattern) different from those of naturally occurring crystals of free (2S,4S)-monatin described in Vleggaar, R. et al., and to demonstrate that the crystal or crystal form of free (2R,4R)-monatin has superior properties in some points of view compared to the crystal of a salt of (2R,4R)-monatin of which the inventors have already found and which is useful as a sweetening agent.

As mentioned above, the naturally occurring monatin has the (2S,4S) steric configuration, but in the context of the present invention, all compounds having the identical chemical structural formula thereto are generically referred to as "monatin." Therefore, the non-naturally occurring stereoisomers of monatin are referred to as a "stereoisomer of naturally occurring monatin," "non-naturally occurring monatin," "(2S,4R)-monatin," "(2R,4S)-monatin," or "(2R,4R)-monatin," or the like. Also, when the (2S,4S)-monatin is considered with these stereoisomers, these may be referred to as "4 kinds of stereoisomers." In particular, naturally occurring monatin is referred to as "monatin," "monatin (a (2S,4S) substance)," or "(2S,4S)-monatin," or the like. Salts of monatin are referred to, e.g., as "potassium salt of (2R,4R)-monatin" or "ammonium salt of (2R,4R)-monatin," or the like. A salt crystal (i.e., a crystal of a salt form) of monatin is referred to, e.g., as "crystal of the potassium salt of (2R,4R)-monatin" or "crystal of the ammonium salt of (2R,4R)-monatin," or the like. A free form (i.e., non-salt) compound of monatin is referred to as "a free compound of (2R,4R)-monatin" or "a free form compound of (2R,4R)-monatin," or the like. Furthermore, a crystal of a free form compound of monatin is referred to as a "crystal of free (2R,4R)-monatin," "crystal of a free compound of (2R,4R)-monatin," or "crystal of free form (2R,4R)-monatin," or the like. In this regard, the term "crystal of free (2R,4R)-monatin" refers to crysatalline (2R, 4R)-monatin which is in the free form, i.e., is not an addition salt, but includes crystals in which the (2R,4R)-monatin exists as a zwitterions, i.e., an internal salt.

Accordingly, it is one object of the present invention to provide novel crystals of monatin.

It is another object of the present invention to provide novel crystals of monatin which are useful as sweeteners.

It is another object of the present invention to provide novel sweetening agents which contain such crystals of monatin.

It is another object of the present invention to provide sweetened foods and beverages which contain such a sweetening agent.

It is another object of the present invention to provide methods of preparing such sweetened foods and beverages.

To solve the above problems, the present inventors have performed an intensive study on the crystals of free (2R,4R)-monatin. First, using a salt crystal of (2R,4R)-monatin with high purity, a crystal of free (2R,4R)-monatin with high purity was prepared according to the methods described in the prior references and the other various methods. Next, the melting point, infrared absorption spectrum, powder X-ray and the like of the resulting crystal were measured and compared with physical properties of the crystal of free (2S,4S)-monatin publicly known in Vleggaar, R. et al.

As a result, it was found that the melting points of all crystal of free (2R,4R)-monatin of which the inventors prepared by various crystallization conditions were nearly identical, but were far from the value of melting point of the crystal of free (2S,4S)-monatin reported in Vleggaar, R. et al. In addition, the observed values of the infrared absorption spectra of the crystal of free (2R,4R)-monatin were different from the values for the crystal of free (2S,4S)-monatin reported in Vleggaar, R. et al. Furthermore, all of the crystals of free (2R,4R)-monatin had the same powder X-ray spectra. Therefore, the crystal of free (2R,4R)-monatin found by the inventors were thought to be a different crystal (form) from the crystal of free (2S,4S)-monatin substance reported in Vleggaar, R. et al., and thus the inventors were led to the conclusion that a novel crystal (form) was discovered.

Additionally, in order to determine usefulness as a sweetening agent, various properties of the crystal of free (2R,4R)-monatin were examined. The water absorption of the crystal of free (2R,4R)-monatin, the crystal of the potassium salt of (2R,4R)-monatin, and the amorphous solid of the potassium salt of (2R,4R)-monatin were examined under a high humidity condition. Consequently, a new finding was obtained that the crystal of free (2R,4R)-monatin scarcely absorbs water and thus is suitable for the intended use as a sweetening agent when storage under high humidity condition is envisioned.

Moreover, it was found to be able to provide sweetening agents or foods and beverages using this crystal of free (2R, 4R)-monatin.

The invention reached completion based on various findings as in the above.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 1:
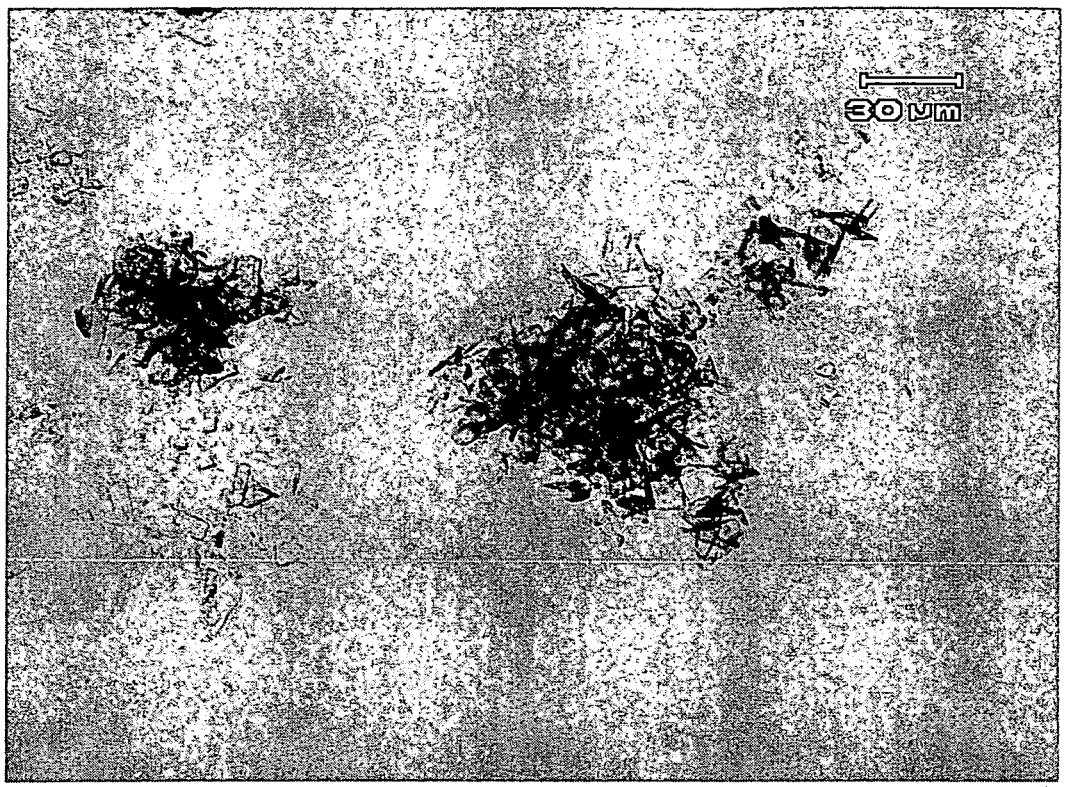
FIG. 1 is an optical micrograph just before separation of a crystallization solution of the crystal of free (2R,4R)-monatin of Comparative Example 1 (magnified at 200 times)

Thus, in a first embodiment, the present invention provides a novel crystal (form) of free (2R,4R)-monatin, which is different from the crystal (form) of free (2S,4S)-monatin, which is publicly known as a naturally occurring stereoisomer; and which is far superior in the degree of sweetness as compared to the crystal of free (2S,4S)-monatin conventionally obtained; and which is excellent as a sweet substance; and which is a practical product form of the sweet substance in terms of being less hygroscopic as compared to the potassium salt crystal and the amorphous solid of (2R,4R)-monatin under high-temperature and high humidity conditions. Thus, the present crystals of free (2R,4R)-monatin have a strong sweetness intensity and may be used as a sweetening agent, and are suitable for a sweetening agent for practical use or an ingredient thereof.

That is, the present invention provides a crystal of free (2R,4R)-monatin. The invention further provides crystals of free (2R,4R)-monatin, an amino acid type sweet substance, and this crystal includes a mixture with other stereoisomers except for a mixture with the crystal of free (2S,4S)-monatin in a molar ratio of 1:1. The other stereoisomers which may be mixed with the free (2R,4R)-monatin include at least one of (2R,4S)-monatin, (2S,4R)-monatin, and (2S,4S)-monatin.

The crystal of free (2R,4R)-monatin may be in the form of a hydrate, a solvate, or the like. Furthermore, a lactone or lactam form which forms by intramolecular cyclization and/or a form in which at least one functional group included is protected may be included within the present crystal of free (2R,4R)-monatin.

With respect to the method for forming the crystal, it is possible to prepare the objective crystal based on the description (Examples and the like) of the present invention by utilizing methods for producing a crystal of a free amino acid commonly used or publicly known, if necessary.

A precursor of monatin which may be used for forming the present crystal may be a monatin derivative having a protecting group for a functional group such as a carboxyl, hydroxyl, amino, or indolyl (indole) group, which is eliminated by the treatment with acid, including salts of monatin (including a crystal form). As the protecting group, it is possible to use any protecting groups regularly used in organic chemistry, particularly amino acid and peptide chemistry, which may be deprotected under acidic conditions.

The (2S,4S) configuration, which is the naturally occurring monatin, and the (2S,4R) configuration, (2R,4R) configuration, and (2R,4S) configuration which are non-naturally occurring monatins are represented by the following structural formulae (1), (2), (3) and (4), respectively.

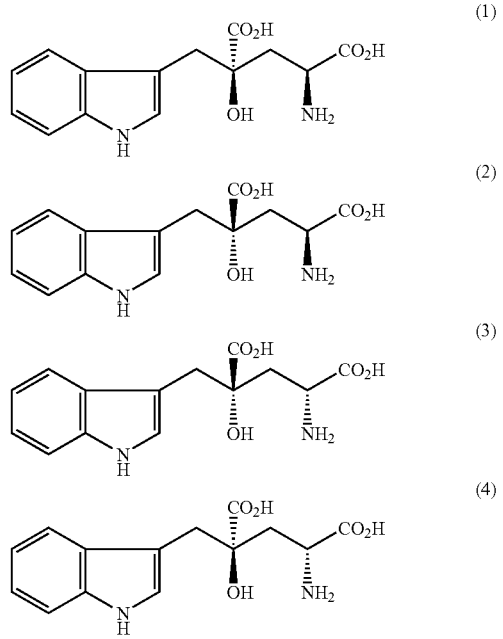

Thus, the crystal of the present invention includes the following crystals, (1) to (8):

(1) As the crystal of free (2R,4R)-monatin, it is possible to employ those which exhibit characteristic X-ray diffraction peaks at diffraction angles (2θ, CuK α-ray) of 5.95°, 17.8°, 19.15°, 21.5°, 23.9°, and 27.75°.

(2) As the crystal of free (2R,4R)-monatin, it is possible to employ those which exhibit characteristic infrared spectrum peaks at 3405, 3086, 1752, 1630, 1558, and 1471 cm$^{-1}$.

(3) As the crystal of free (2R,4R)-monatin, it is possible to employ those having a melting point of 165° C. to 180° C., preferably of 169° C. to 177° C.

(4) The crystal of free (2R,4R)-monatin may be a mixture of crystals with at least one crystal of another stereoisomer of a free compound of monatin. As the other stereoisomer of free compound of monatin, (2R,4S)-monatin and (2S,4R)-monatin are more preferable in terms of high sweetness intensity, and (2R,4S)-monatin is most preferable.

(5) The crystal of free (2R,4R)-monatin of the present invention can also be used as a mixture of crystals with crystals of naturally occurring free (2S,4S)-monatin. In this case, however, the composition ratio of the crystals of free (2R,4R)-monatin to the crystals of free (2S,4S)-monatin may be of any molar ratio other than 1:1, and in terms of sweetness intensity, it is preferable to maintain the amount of crystals of free (2R,4R)-monatin preferably at about 70% by weight based on the total weight of the monatin.

(6) The crystal of free (2R,4R)-monatin of the present invention may have the monatin stereoisomer (including forms such as hydrate and solvate) at a chemical purity of preferably at least about 90%, more preferably about 95%, and still preferably at least about 98%.

(7) Also, the above non-naturally occurring stereoisomer crystal of the present invention may have an optical purity of preferably at least about 90%, more preferably at least about 94%, and still preferably at least about 98%. For example, it is possible to include an composition with high optical purity containing the crystal of free (2R,4R)-monatin (including forms such as hydrate, solvate and salt mixture thereof) at 98% or more.

(8) As the above crystal of free (2R,4R)-monatin of the present invention, it is possible to employ those which exhibit a sweetness intensity of preferably at least about 200 times, and more preferably at least about 1000 times that of sucrose at a practical use concentration of 5 to 10%.

The crystal of a free compound of monatin can be used in the form of a hydrate, a solvate, and the like, and further can be contained (used) in a form of a lactone or a lactam which forms by intramolecular cyclization and/or in a form in which at least one functional group included is protected.

Also in this case, in a crystal of a free compound of monatin, it is possible to prepare one having a sweetness intensity of a mixed crystal of preferably at least about 200 times, and more preferably at least about 1000 times that of the above sucrose at a practical use concentration as preferable one.

In another embodiment, the present invention provides a sweetening agent which is characterized by containing the above crystal of free (2R,4R)-monatin of the present invention, including those of (1) to (8) mentioned above.

The sweetening agent may comprise a carrier and/or a bulking agent and the like for sweetening agents.

Any carrier or bulking agent known to be used for sweetening agents and to be developed hereafter therefor may be comprised in the present sweetening agent. Additionally, of course, additives capable of being used for sweetening agents may also be included. The sweetening agent is used for animals, for example, for mammals, and particularly for humans.

In another embodiment, the present invention provides products such as foods and beverages to which sweetness has been imparted, characterized by containing the above crystal of free (2R,4R)-monatin of the present invention, including those of (1) to (8) mentioned above.

The crystals of the present invention may also be used as at least a part of the sweetening agent for products for animals which require sweetness, particularly for foods and beverages for humans which require sweetness. Additionally, the crystals of the present invention may be used for oral hygienic purposes such as in toothpaste, mouthwash, and drugs, or other products for oral use to which sweetness is to be imparted.

At least one other sweetening agent ingredient (sweetener), particularly sugars, and other artificial and naturally occurring sweeteners can be contained in the above sweetening agent and the sweetened products such as foods and beverages, of the present invention. For example, sucrose, aspartame, acesulfame K, sucralose, saccharin, stevioside, xylose, trehalose, sorbitol, maltitol, and the like can be contained in the present sweetening agents.

Hereinafter, modes for carrying out the invention are described.

In Vleggaar, R. et al., crystals of free (2S,4S)-monatin (fine rosettes of a needle-like crystal) are obtained by dissolving 100 mg of a salt of (2S,4S)-monatin in water (1 cm$^3$), adding acetic acid (1 cm$^3$) and ethanol (96%,5 cm$^3$), and leaving it overnight at room temperature. The melting point and infrared spectral spectrum of the crystals are reported as follows:

m.p.—216 to 220° C.;
$v_{max}$—(KBr)/cm$^{-1}$ 3396(NH2), 3020, 1580 (CO$_2$H), and 1540.

In Holzapfel, C. W. et al., it is reported that 80 mg of a racemic crystal of free compound of (2S,4S)-monatin and free compound of (2R,4R)-monatin is obtained by dissolving 150 mg of the ammonium salt of four stereoisomer mixtures of monatin in 1 ml of water, adding 0.1 ml of acetic acid to yield a crystal, and repeating the same crystallization twice. The melting point of the crystal is reported as follows.

m.p.—212 to 214° C.

Monatin of the (2R,4R) configuration, (2R,4S) configuration, (2S,4R) configuration, (2S,4S) configuration, and mixtures of the four stereoisomers can be synthesized according to the methods described in Amino, Y. et al., WO 2003045914 A1 and PCT International Application Publication No. 03/059865 (Kawahara, S. et al., WO 2003059865 A1) of which the inventors have developed, but the methods for synthesizing monatin comprising the various stereoisomers are not limited to these methods.

Crystals of various salts of (2R,4R)-monatin synthesized according to the methods mentioned above were exchanged to crystals of free (2R,4R)-monatin using the methods described in Vleggaar, R. et al. and Holzapfel, C. W. et al., cited above, or methods where the conditions thereof were slightly modified.

To obtain the crystals of free (2R,4R)-monatin, it is not necessary to use crystals of a salt of (2R,4R)-monatin with high purity as the starting material. As mentioned above, acid may be added directly into a synthesis reaction solution to acidify, or it is also possible to obtain the crystals of free (2R,4R)-monatin by dissolving a synthesized crude product in an aqueous solution and subsequently acidifying the solution.

Also, it is possible to obtain the crystals of free (2R,4R)-monatin by crystallizing under acidic conditions using an amorphous solid salt of (2R,4R)-monatin, (2R,4R)-monatin containing another stereoisomer, (2R,4R)-monatin in which the amino group is protected with a t-butoxycarbonyl group, and the like.

It is also possible to obtain the crystals of free (2R,4R)-monatin by subjecting a lactone or lactam of (2R,4R)-monatin formed by intramolecular cyclization to a ring opening reaction (hydrolytic reaction) under basic conditions and subsequently making the reaction solution acidic.

According to the present invention, all of the crystals of free (2R,4R)-monatin newly prepared by the various methods had melting points at temperatures of about 169° C. to 173° C., which nearly conformed to those determined by inventors in Comparative Example 1 in Amino, Y. et al., WO 2003045914 A1. Meanwhile, the melting points were far from the melting point of 216° C. to 220° C. of the crystal of naturally occurring free (2S,4S)-monatin described in Vleggaar, R. et al. and the melting point of 247° C. to 265° C. (decomposition) of crystal of the naturally occurring free (2S,4S)-monatin described in van Wyk, P. J. et al., ZA 87/4288. That is, the crystal (form) of free (2R,4R)-monatin of the present invention has a physical property which is clearly different from that of the crystal (form) of free (2S,4S)-monatin described in Vleggaar, R. et al.

One reason why the physical properties of the crystals of free (2R,4R)-monatin prepared by the inventors do not conform to those of the crystals of free (2S,4S)-monatin in Vleggaar, R. et al. is the possibility that the crystal of free (2S,4S)-monatin in Vleggaar, R. et al. is not optically pure. As described below, the inventors separately prepared a 1:1 mixture of crystals of free (2R,4R)-monatin and crystals of free (2S,4S)-monatin, and found that its melting point is approximately 225° C. to 229° C., which is close to the melting point of 212° C. to 214° C. of a racemic crystal of free (2R,4R)-monatin and (2S,4S)-monatin reported in Holzapfel, C. W. et al. Furthermore, the melting point of 216° C. to 220° C. of the crystal of naturally occurring free (2S,4S)-monatin in Vleggaar, R. et al. is closer to these values than the melting point of approximately 169° C. to 173° C. of the crystal of free (2R,4R)-monatin of the present invention. Also by comparing the sweetness intensity, (2S,4S): 50 times, (2R,4R): 2700 times, both at an optical purity of 99% or more, of monatin stereoisomers demonstrated by the inventors in Amino, Y. et al., WO 2003045914 A1 with the sweetness intensity (800 to 1400 times) of the naturally occurring monatin described in Vleggaar, R. et al., it is suggested that the crystal of free (2S,4S)-monatin in Vleggaar, R. et al. is not optically pure. In such a case, it can be said that the optically pure crystal of a free monatin substance was isolated and its various physical properties were demonstrated by the inventors for the first time.

In the infrared absorption spectrum of the present crystal of free (2R,4R)-monatin, no characteristic peak was detected at 3020, 1580 and 1540 cm$^{-1}$ which are the characteristic absorption peaks of the crystal of free (2S,4S)-monatin described in Vleggaar, R. et al. That is, the crystal of free (2R,4R)-monatin of the present invention is a crystal having characteristic infrared absorption spectrum peaks at 3405, 3086, 1752, 1630, 1558, and 1471 cm$^{-1}$.

The powder X-ray diffraction patterns of all the prepared crystals of free (2R,4R)-monatin showed the same spectrum pattern. That is, the crystals of free (2R,4R)-monatin of the present invention is a crystal which exhibits characteristic X-ray diffraction peaks at diffraction angles (2θ, CuK α ray) of 5.95°, 17.8°, 19.15°, 21.5°, 23.9°, and 27.75°.

It was identified that the sweetness intensity (degree of sweetness) of the present crystals of free (2R,4R)-monatin is about 2500 times that of an aqueous solution of 5% sucrose. This sweetness intensity is nearly equivalent to the sweetness intensity (about 2700 times) of the crystals of the sodium salt of (2R,4R)-monatin evaluated by the inventors in Amino, Y. et al., WO 2003045914 A1.

The purity of the present crystals of free (2R,4R)-monatin prepared in the examples was determined by high performance liquid chromatography, to be 99% or more.

The $^1$H-NMR spectrum and mass spectrogram of the present crystal of free (2R,4R)-monatin supported the structure of monatin.

Figure 5:
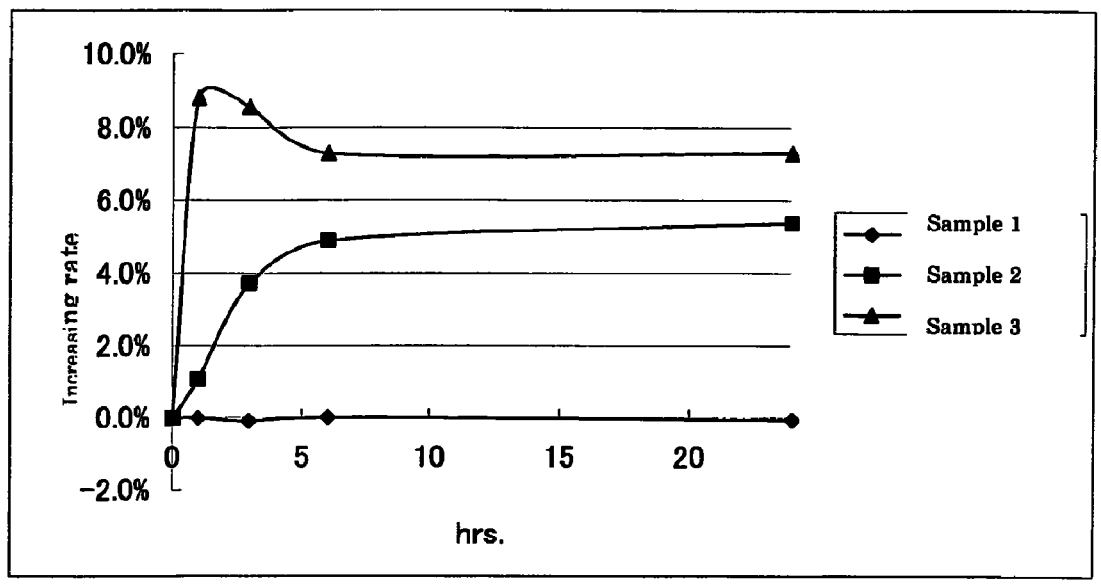
FIG. 5 is a graph showing the results of a hygroscopic property test (25° C., humidity 95%) of the crystal of free (2R,4R)-monatin (sample 1), the crystal of the potassium salt of (2R,4R)-monatin monohydrate (sample 2), and the amorphous potassium salt of (2R,4R)-monatin (sample 3) of Example 2 (vertical axis: weight increase percentage (% by weight); horizontal axis: retention time (unit; hour)

The present crystals of free (2R,4R)-monatin, crystals of the potassium salt of (2R,4R)-monatin monohydrate, and the amorphous solid of the potassium salt of (2R,4R)-monatin of Amino, Y. et al., WO 2003045914 A1 were placed under a 95% high humidity condition, and the amounts of absorbed water were compared (see, Table 1 and FIG. 5). As a result, the amorphous solid of the potassium salt of (2R,4R)-monatin and the crystals of the potassium salt of (2R,4R)-monatin monohydrate absorbed 7.3 wt. % and 5.4 wt. % water, respectively after 24 hours. On the contrary, it was found that the crystals of free (2R,4R)-monatin has the preferable property for a sweetening agent in terms of no water absorption even under the condition of high humidity.

When the crystals of free (2R,4R)-monatin (including hydrate, solvate, and the like) of the present invention are used as a sweetening agent, a carrier and/or an bulking agent may be used if necessary. For example, it is possible to use any carrier, bulking agent, and the like which are conventionally used or known for sweetening agents.

The crystals of free (2R,4R)-monatin (including hydrate, solvate, and the like) of the present invention can be used as a sweetening agent or a sweetening agent ingredient, and also can be used as the sweetening agent for various products including foods and beverages which require sweetness to be imparted, such as confectioneries and chewing gum, hygienic products, cosmetics, drugs, and products for animals other than humans. Furthermore, the crystals of free (2R,4R)-monatin of the present invention can be used as the mode of a product which contains the crystal of free (2R,4R)-monatin of the present invention and to which sweetness is imparted, and in a method for imparting sweetness to the product to which sweetness should be imparted. Such methods for the use thereof can be performed according to the conventional methods commonly used as the method for the use of sweetening agents and the other methods publicly known.

Other features of the invention will become apparent in the course of the following descriptions of exemplary embodiments which are given for illustration of the invention and are not intended to be limiting thereof.

EXAMPLES $^1$H-NMR spectra and MS spectra were measured using a Bruker AVANCE 400 (400 MHz) and Thermo Quest TSQ 700, respectively. Powder X-ray diffraction analysis was performed on a PW3050 supplied from Phillips. The melting point measurements were performed using a MICRO MELTING POINT APPARATUS of Yanaco. Infrared absorption spectra were determined with a Spectrum One FT-IR Spectrometer of Perkin Elmer.

Comparative Example 1

Preparation of Crystals of Free (2R,4R)-monatin (I) as Described in Amino, Y. et al., WO 2003045914 A1.

After dissolving 0.5 g of the ammonium salt of (2R,4R)-monatin (optical purity of 99% or more) in 10 ml of an aqueous solution of 50% acetic acid, 25 ml of ethanol was added during one hour at 25° C. The solution was further stirred at 25° C. for 4.5 hours. Crystals were separated from the resultant crystallization solution and subsequently a wet product was dried in a vacuum dryer at reduced pressure to yield 0.38 g of crystals of free (2R,4R)-monatin.

Melting point: 175.2 to 176.1° C.

The result of remeasuring the melting point of the same sample was as follows.

Melting point: 171.5 to 172.7° C.

An optical micrograph taken just before the separation of the crystals of free (2R,4R)-monatin from the crystallization solution is illustrated in FIG. 1 (magnified at 200 times).

Figure 2:
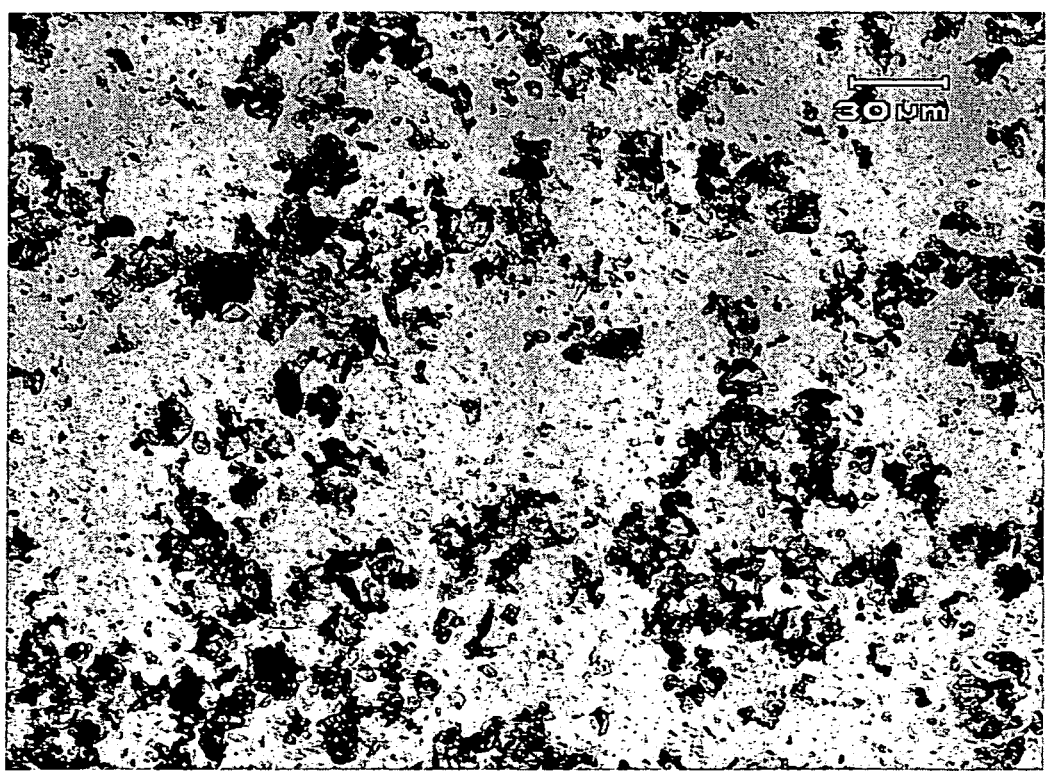
FIG. 2 is an optical micrograph the crystal of free (2R,4R)-monatin of Comparative Example 1 (magnified at 200 times) after drying.

An optical micrograph of the crystals of free (2R,4R)-monatin after drying is illustrated in FIG. 2 (magnified at 200 times).

Figure 3:
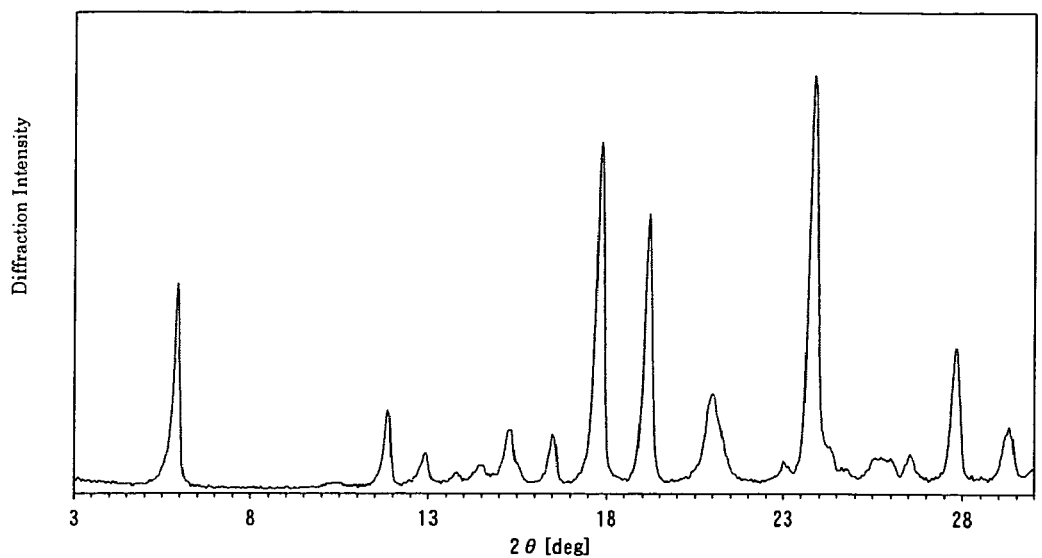
FIG. 3 is a powder X-ray diffraction pattern of the crystal of free (2R,4R)-monatin of Comparative Example 1 after drying.

A powder X-ray diffraction pattern of the crystals of free (2R,4R)-monatin after drying is shown in FIG. 3. The crystals exhibited characteristic X-ray diffraction peaks at diffraction angles (2θ, CuK α ray) of 5.9°, 17.9°, 19.2°, 23.9°, and 27.8°.

Example 1

1.05 mg of crystals of free (2R,4R)-monatin described in the above Comparative Example 1 were dissolved in 20 ml of ion-exchanged water. A solution was prepared by diluting this solution 2.5 times. The sweetness of this aqueous solution of the free compound of (2R,4R)-monatin was compared with that of an aqueous solution of 5% sucrose separately prepared. It was found that both solutions have nearly equivalent sweetness intensity.

The $^1$H-NMR of the crystals of free (2R,4R)-monatin described in the above Comparative Example 1 was as follows (400 MHz, $D_2O$+ a drop of an aqueous solution of 5% ammonia).

1.87 (1H, dd), 2.50 (1H, d), 3.00 (1H, d, J=14.4 Hz), 3.20 (1H, d, J=14.4 Hz), 3.46 (1H, d), 7.07 (1H), 7.15 (2H, m), 7.41 (1H, d, J=8.0 Hz), 7.65 (1H, d, J=8.0 Hz).

The MS spectrum was as follows.

ESI-MS: 291 (M–H)$^-$.

The infrared absorption spectrum was as follows ($v_{max}$ (KBr)/cm$^{-1}$).

3405, 3086, 1752, 1630, 1558, 1471, 1404, 1330, 1219, 1166, 1121, 740.

Figure 4:
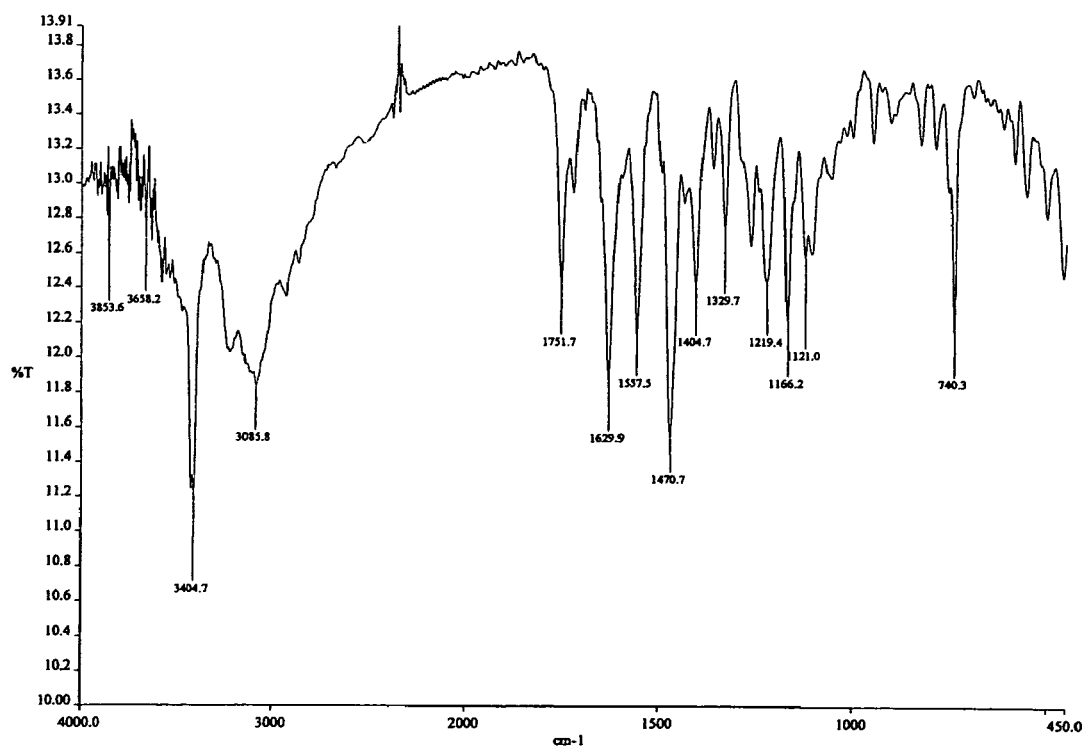
FIG. 4 is an infrared absorption spectrum of the crystal of free (2R,4R)-monatin of Example 1.

The infrared absorption spectrum of the crystals of free (2R,4R)-monatin is shown in FIG. 4.

Example 2

Hygroscopic Property Test

The crystals of free (2R,4R)-monatin (sample 1) prepared in Comparative Example 1, crystal of the potassium salt of (2R,4R)-monatin monohydrate (sample 2), and an amorphous solid of the potassium salt of (2R,4R)-monatin (sample 3) separately prepared were weighed out in an amount of 0.5 g, respectively, each was placed in a petri dish, and stored (retained) under a high humidity condition of 95% and a temperature of 25° C. After retention times of 1, 3, 6 and 24 hours, the weight of each sample was measured. The relationship of the retention time, sample weight, and weight change (amount of absorbed water) is shown in the following Table 1 and in FIG. 5. The measuring conditions were as follows.

Apparatus name: HIFLEX TH401 supplied from ETAC.

Storing condition: 25° C., humidity of 95%.

Sample container: diameter of 25 cm, glass petri dish.

TABLE 1

Relationship of retention time, sample weight and weight change (absorbed water amount).

| Retention time (hrs.) | Sample 1 | | Sample 2 | | Sample 3 | |
|---|---|---|---|---|---|---|
| | Weight (g) | Increase percentage (%) | Weight (g) | Increase percentage (%) | Weight (g) | Increase percentage (%) |
| 0 | 0.5000 | 0.00 | 0.5007 | 0.00 | 0.5014 | 0.00 |
| 1 | 0.5000 | 0.00 | 0.5061 | 1.08 | 0.5456 | 8.82 |
| 3 | 0.4996 | 0.00 | 0.5193 | 3.71 | 0.5444 | 8.58 |
| 6 | 0.5001 | 0.00 | 0.5252 | 4.89 | 0.5383 | 7.30 |
| 24 | 0.4997 | 0.00 | 0.5277 | 5.39 | 0.5380 | 7.30 |

Example 3

Preparation of Crystals of Free (2R,4R)-monatin (II)

100 mg of the sodium salt of (2R,4R)-monatin (with 0.1 molar equivalent of ethanol) (0.313 mmol, optical purity of 99% or more) was dissolved in 5 ml of water, and the contained ethanol was eliminated by concentration under reduced pressure. The residue was dissolved in 2 ml of water, and an aqueous solution of 1N acetic acid was added to adjust the pH of the solution to 3 to 4. Crystals were precipitated by leaving the solution overnight at room temperature. The pH of the solution was adjusted again to 3 to 4, and the solution was left overnight to further precipitate the crystals. By collecting the precipitated crystal by filtration and drying, 77 mg (0.263 millimol) of crystals of free (2R,4R)-monatin were obtained at a yield of 84.0%. The purity of the resultant crystal was tested by HPLC and found to be 99% or more.

Melting point: 169.4 to 171.2° C.

The infrared absorption spectrum of the crystals obtained in Example 3 showed characteristics peak at 3404, 3083, 1750, 1630, 1558, 1472, 1406, 1330, 1220, 1166, 1122, and 740 $cm^{-1}$ as is nearly the case with Example 2 ($v_{max}$(KBr)/$cm^{-1}$).

Example 4

Preparation of Crystal of Free (2R,4R)-monatin (III)

Crystals were prepared as is the case of Example 3, except that an aqueous solution of 1N hydrochloric acid was used in place of the aqueous solution of 1N acetic acid. 71 mg (0.243 mmol) of crystals of free (2R,4R)-monatin were obtained at a yield of 77.6%. The purity of the resultant crystals was tested by HP LC, and found to be 99% or more.

Melting point: 170.7 to 172.1° C.

Example 5

Preparation of Crystals of Free (2R,4R)-monatin Substance (IV)

250 mg (0.782 mmol, optical purity of 99% or more) of the sodium salt of (2R,4R)-monatin (with 0.1 molar equivalent of ethanol) was dissolved in 10 ml of water, and the contained ethanol was eliminated by concentration under reduced pressure. The residue was dissolved in 3 ml of water, and an aqueous solution of 1N sulfuric acid was added to adjust the pH of the solution to 3 to 4. The solution was stirred for one hour at room temperature to precipitate crystals. The pH of the solution was adjusted again to 3 to 4, and the solution was stirred for one hour at room temperature to further precipitate crystals. By collect the precipitated crystal by filtration and drying, 206 mg (0.705 mmol) of crystals of free (2R,4R)-monatin were obtained at a yield of 90.2%.

Melting point: 169.8 to 171.5° C.

Example 6

Preparation of Crystals of Free (2R,4R)-monatin Substance (V)

After dissolving 3.5 g (11.3 mmol, optical purity of 99% or more) of the ammonium salt of (2R,4R)-monatin in 70 ml of an aqueous solution of 50% acetic acid, 175 ml of ethanol was added dropwise over one hour at 25° C. The solution was further stirred for 4.5 hours at 25° C., and the obtained crystals were collected by filtration and dried to yield 2.75 g of the crystals of free (2R,4R)-monatin.

Figure 6:
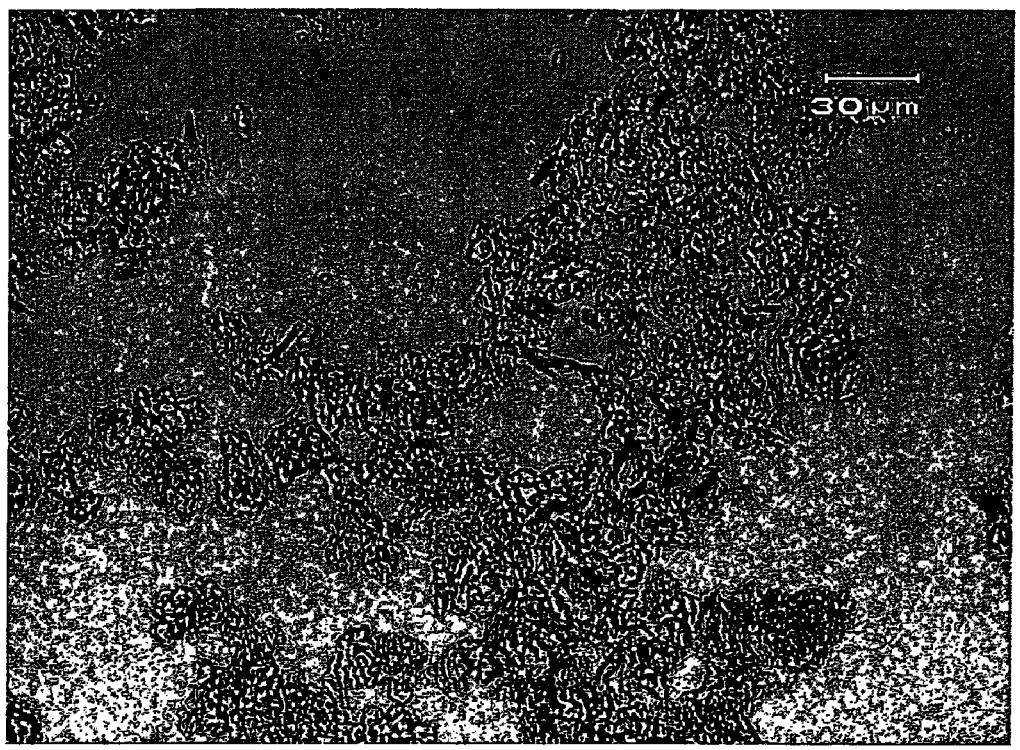
FIG. 6 is an optical micrograph of the crystal of free (2R, 4R)-monatin of Example 6 (magnified at 200 times)

An optical micrograph of the crystals obtained in Example 6 is illustrated in FIG. 6 (magnified at 200 times).

Figure 7:
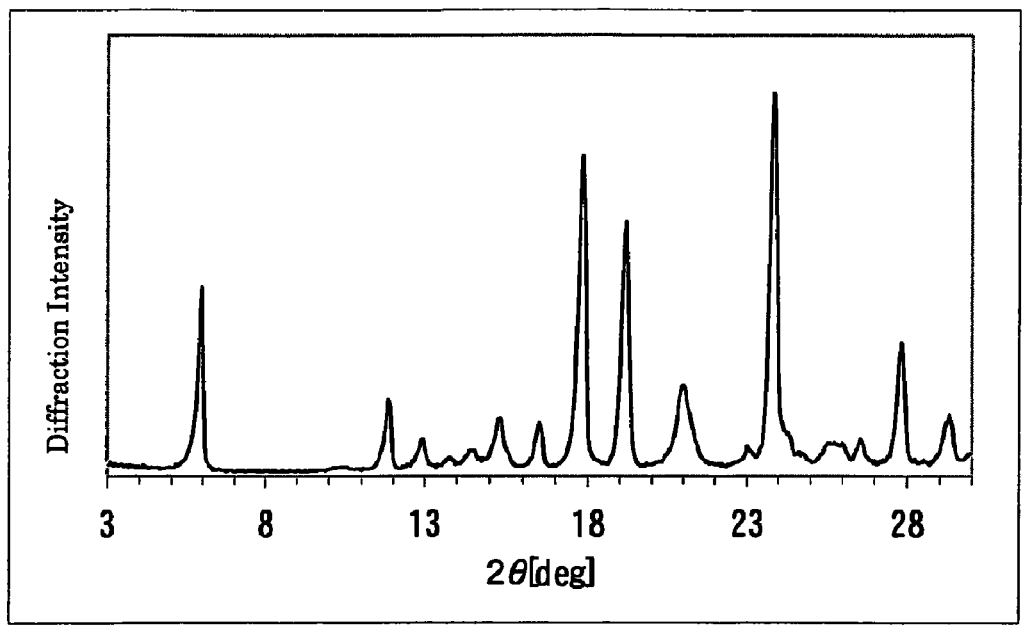
FIG. 7 is a powder X-ray diffraction pattern of the crystal of free (2R,4R)-monatin of Example 6 after drying.

The powder X-ray diffraction pattern of the crystals obtained in Example 6 is shown in FIG. 7. The crystals exhibited characteristic X-ray diffraction peaks at diffraction angles (2θ, CuK α ray) of 5.95°, 17.8°, 19.15°, 21.05°, 23.9°, and 27.75°.

Example 7

Preparation of Crystals of Free (2R,4R)-monatin (VI)

After dissolving 0.5 g (1.44 mmol, optical purity of 99% or more) of the potassium salt of (2R,4R)-monatin in 10 ml of water, 1.44 ml of 1N hydrochloric acid was added at 50° C. The solution was stirred for 20 min at 50° C., then cooled to 10° C. at 10° C./hr, and the obtained crystals were collected by filtration and dried to yield 0.41 g of the crystals of free (2R,4R)-monatin.

Melting point: 170.0 to 172.1° C.

Figure 8:
FIG. 8 is an optical micrograph of the crystal of free (2R, 4R)-monatin of Example 7 after drying (magnified at 200 times)

An optical micrograph of the crystals obtained in Example 7 is illustrated in FIG. 8 (magnified at 200 times).

The powder X-ray diffraction pattern of the crystals obtained in Example 7 exhibited characteristic X-ray diffraction peaks at diffraction angles (2θ, CuK α ray) of 5.95°, 17.8°, 19.15°, 21.05°, 23.9°, and 27.75° as in the case with Example 6.

Example 8

Preparation of Crystals of Free (2R,4R)-monatin (VII)

After dissolving 0.5 g (1.44 mmol, optical purity of 99% or more) of the potassium salt of (2R,4R)-monatin in 10 ml of water, 1.44 ml of 1N hydrochloric acid was added at 10° C. By stirring for 4.5 hours at 10° C., filtering, and drying the obtained crystals, 0.42 g of crystals of free (2R,4R)-monatin were obtained.

Melting point: 171.5 to 173.2° C.

Figure 9:
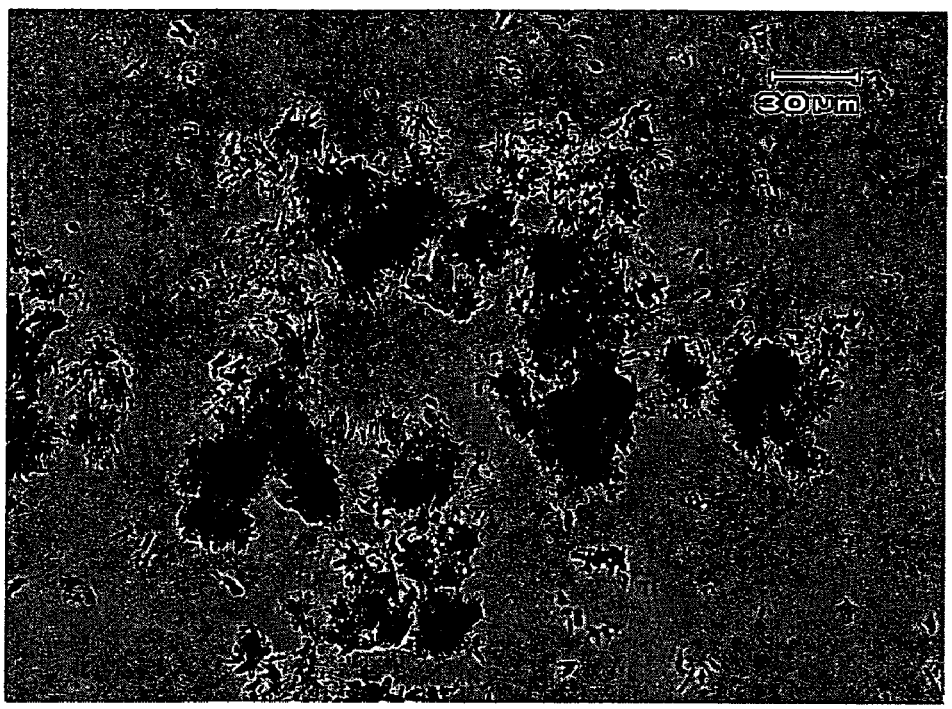
FIG. 9 is an optical micrograph of the crystal of free (2R, 4R)-monatin of Example 8 (magnified at 200 times)

An optical micrograph of the crystals obtained in Example 8 is illustrated in FIG. 9 (magnified at 200 times).

The powder X-ray diffraction pattern of the crystals obtained in Example 8 exhibited characteristic diffraction X-ray peaks at diffraction angles (2θ, CuK α ray) of 5.95°, 17.8°, 19.15°, 21.05°, 23.9°, and 27.75° as in the case with Example 6.

Reference Example

Preparation of Crystals of a 1:1 Mixture of Free (2R,4R)-monatin and Free (2S,4S)-monatin A 1:1 by weight mixture (1.00 g) (3.23 mmol, purity of 99% or more) of the ammonium salt of (2R,4R)-monatin and the ammonium salt of (2S,4S)-monatin was dissolved in 20 ml of water and concentrated under reduced pressure. The residue was dissolved in 5 ml of water, and an aqueous solution of 1N acetic acid was added to adjust the pH of the solution into 3 to 4. The solution was stirred for 30 min at room temperature to precipitate crystals. Again, the pH of the solution was adjusted to 3 to 4, and the solution was stirred for 30 min at room temperature to further precipitate the crystals. The precipitated crystal were collected by filtration and dried, to obtain 778 mg (2.66 millimol) of the crystals of a 1:1 mixture of free (2R,4R)-monatin and free (2S,4S)-monatin at a yield of 82.4%.

Melting point: 225 to 229° C. (decomposition).

Figure 10:
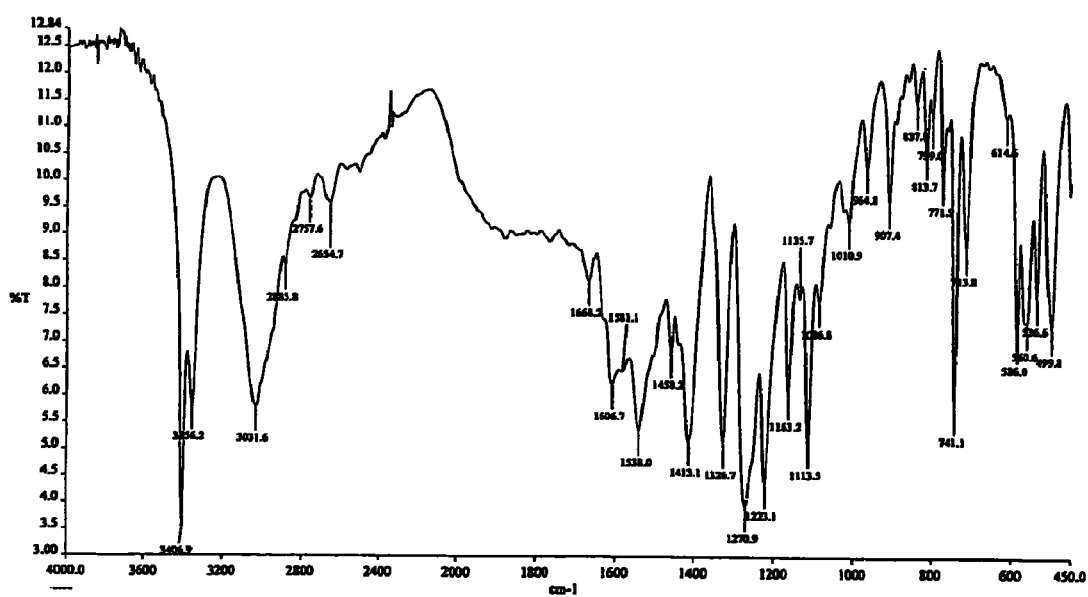
FIG. 10 is an infrared absorption spectrum of a 1:1 mixture of the crystal of free (2R,4R)-monatin and the crystal of free (2S,4S)-monatin of the Reference Example after drying.

The infrared absorption spectrum of the crystals obtained in Reference Example is illustrated in FIG. 10. The crystals exhibited characteristic absorption peaks at 3407, 3356, 3032, 2654, 1668, 1607, 1581, 1538, 1413, 1327, 1271, 1223, 1163, 1114, and 741 cm$^{-1}$ ($v_{max}$ (KBr)/cm$^{-1}$).

Figure 11:
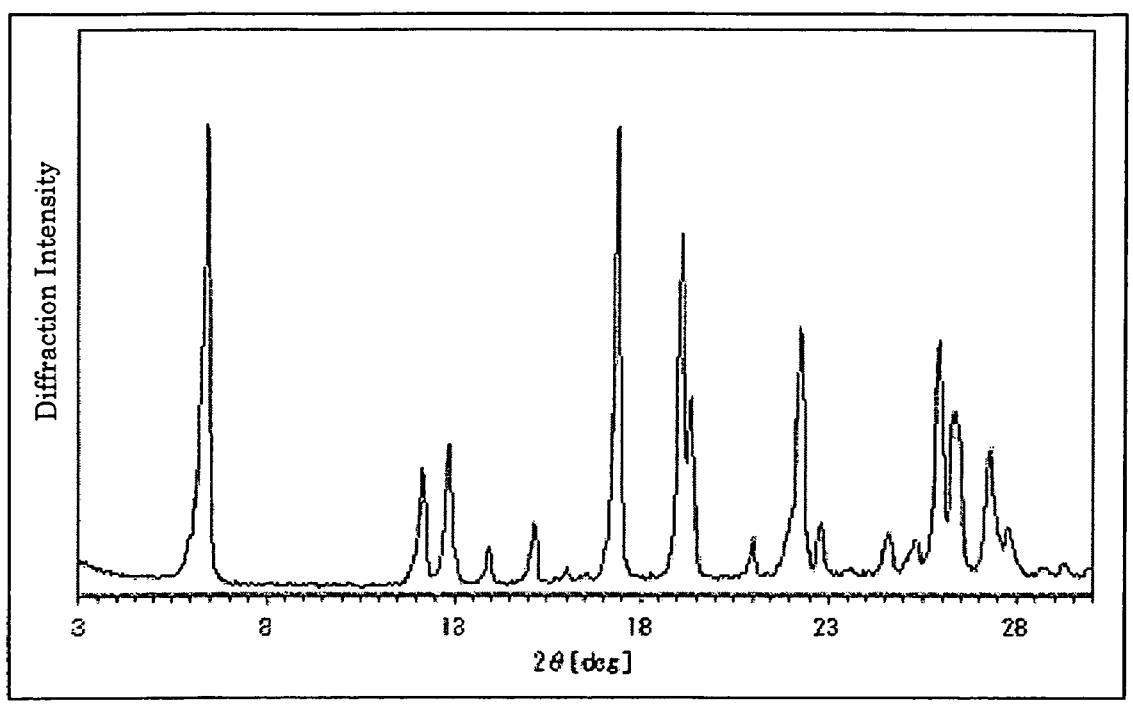
FIG. 11 is a powder X-ray diffraction pattern of the 1:1 mixture of the crystal of free (2R,4R)-monatin and the crystal of free (2S,4S)-monatin of the Reference Example after drying.

The powder X-ray diffraction pattern of the crystals obtained in the Reference Example is shown in FIG. 11. The crystals exhibited characteristic X-ray diffraction peaks at diffraction angles (2θ, CuK α ray) of 6.4°, 12.9°, 17.4°, 19.1°, 22.3°, and 25.9°.

According to the present invention, there are provided products such as foods and beverages to which sweetness is imparted by the use of a novel sweet substance, a crystal of free (2R,4R)-monatin as an active ingredient. The crystal of free (2R,4R)-monatin is excellent in terms of lows water absorption particularly even under high humidity conditions, exhibits a strong sweetness intensity, and exerts excellent flavor identification properties as a sweetening agent. Furthermore, according to the present invention, there is provided a novel sweet substance, a crystal of free (2R,4R)-monatin, which has excellent properties as a sweetening agent or an ingredient thereof, or a sweetness imparting ingredient for foods and beverages and the like. Therefore, the invention is highly useful industrially, particularly in the food field.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. Crystalline free (2R, 4R)-monatin,
   which has a sweetness intensity of at least 1000 times that of sucrose, and
   which exhibits X-ray diffraction peaks at diffraction angles (2θ, CuK α ray) of 5.95°, 17.8°, 19.15°, 21.5°, 23.9°, and 27.75°.

2. Crystalline free (2R, 4R)-monatin according to claim 1, which is isolated and purified.

3. Crystalline free (2R, 4R)-monatin according to claim 1, which has a chemical purity of at least 95%.

4. A sweetening agent, which comprises crystalline free (2R, 4R)-monatin according to claim 1 and a carrier and/or an bulking agent.

5. A sweetening agent according to claim 4, which further comprises at least one ingredient selected from the group consisting of sucrose, aspartame, acesulfame K, sucralose, saccharin, stevioside, xylose, trehalose, sorbitol, and maltitol.

6. A sweetening agent, which comprises crystalline free (2R, 4R)-monatin according to claim 3 and a carrier and/or an bulking agent.

7. A sweetening agent according to claim 6, which further comprises at least one ingredient selected from the group consisting of sucrose, aspartame, acesulfame K, sucralose, saccharin, stevioside, xylose, trehalose, sorbitol, and maltitol.

8. A sweetened food, which comprises crystalline free (2R, 4R)-monatin according to claim 1.

9. A sweetened food according to claim 8, which further comprises at least one ingredient selected from the group consisting of sucrose, aspartame, acesulfame K, sucralose, saccharin, stevioside, xylose, trehalose, sorbitol, and maltitol.

10. A method of sweetening a food, comprising:
    (a) adding crystalline free (2R, 4R)-monatin according to claim 1 to a food.

11. A method of sweetening a food, comprising:
    (a) adding a sweetening agent according to claim 4 to a food.

12. A sweetened beverage, which comprises crystalline free (2R, 4R)-monatin according to claim 1.

13. A sweetened beverage according to claim 12, which further comprises at least one ingredient selected from the group consisting of sucrose, aspartame, acesulfame K, sucralose, saccharin, stevioside, xylose, trehalose, sorbitol, and maltitol.

14. A method of sweetening a beverage, comprising:
    (a) adding crystalline free (2R, 4R)-monatin according to claim 1 to a beverage.

15. A method of sweetening a beverage, comprising:
    (a) adding a sweetening agent according to claim 4 to a beverage.

16. An oral hygiene product, which comprises crystalline free (2R, 4R)-monatin according to claim 1.

17. An oral hygiene product according to claim 16, which further comprises at least one ingredient selected from the group consisting of sucrose, aspartame, acesulfame K, sucralose, saccharin, stevioside, xylose, trehalose, sorbitol, and maltitol.

18. An oral hygiene product according to claim 16, wherein said oral hygiene product is selected from the group consisting of toothpaste, mouthwash, and oral drugs.

19. A method of sweetening an oral hygiene product, comprising:
    (a) adding crystalline free (2R, 4R)-monatin according to claim 1 to an oral hygiene product.

20. An method according to claim 19, wherein said oral hygiene product is selected from the group consisting of toothpaste, mouthwash, and oral drugs.

21. A method of sweetening an oral hygiene product, comprising:

(a) adding a sweetening agent according to claim 4 to an oral hygiene product.

22. An method according to claim 21, wherein said oral hygiene product is selected from the group consisting of toothpaste, mouthwash, and oral drugs.

23. Crystalline free (2R, 4R)-monatin according to claim 1, which has an optical purity of at least 90%.

24. Crystalline free (2R, 4R)-monatin according to claim 1, which has an optical purity of at least 94%.

25. Crystalline free (2R, 4R)-monatin according to claim 1, which has an optical purity of at least 98%.

* * * * *